US009301732B2

United States Patent
Tonomura et al.

(10) Patent No.: US 9,301,732 B2
(45) Date of Patent: *Apr. 5, 2016

(54) ULTRASONIC DIAGNOSTIC ARRANGEMENTS SELECTING PARAMETERS FOR SELECTING RELEVANT ESTIMATION DATA FOR CLASSIFYING AN ELASTICITY IMAGE

(71) Applicant: Hitachi Medical Corporation, Tokyo (JP)

(72) Inventors: Akiko Tonomura, Tokyo (JP); Tsuyoshi Mitake, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/220,689

(22) Filed: Mar. 20, 2014

(65) Prior Publication Data

US 2014/0206997 A1 Jul. 24, 2014

Related U.S. Application Data

(62) Division of application No. 12/935,694, filed as application No. PCT/JP2009/056703 on Mar. 31, 2009, now Pat. No. 8,718,339.

(30) Foreign Application Priority Data

Mar. 31, 2008 (JP) ................................. 2008-089328

(51) Int. Cl.
*G06K 9/00* (2006.01)
*A61B 8/00* (2006.01)
(Continued)

(52) U.S. Cl.
CPC . *A61B 8/463* (2013.01); *A61B 8/08* (2013.01); *A61B 8/0858* (2013.01); *A61B 8/13* (2013.01);
(Continued)

(58) Field of Classification Search
None
See application file for complete search history.

(56) References Cited

U.S. PATENT DOCUMENTS

2004/0260180 A1* 12/2004 Kanai et al. .................... 600/449
2007/0093716 A1    4/2007 Radulescu
(Continued)

FOREIGN PATENT DOCUMENTS

EP    1 421 905 A1    5/2004
EP    1 665 987 A1    6/2006
(Continued)

OTHER PUBLICATIONS

Kadah, Yasser M. et al., "Classification Algorithms for Quantitative Tissue Characterization of Diffuse Liver Disease from Ultrasound Images", IEEE Transactions on Medical Imaging, IEEE Service Center, Piscataway, NJ, US, vol. 15, No. 4, Aug. 1, 1996.
(Continued)

*Primary Examiner* — Tahmina Ansari
(74) *Attorney, Agent, or Firm* — Jones Robb PLLC (57) ABSTRACT

Ultrasonic diagnostic apparatus including: a tomogram constructing means; an elasticity information calculating means; an elasticity image constructing means; a display means; an estimation data generating means configured to generate estimation data for estimating the characteristic of a biomedical tissue on the basis of the elasticity image; an estimation data selecting means configured to select at least one parameter used for the estimation of the characteristic of the biomedical tissue and to make the selected parameter displayed on the display means, an analyzing means configured to analyze the elasticity image using at least one parameter selected by the estimation data selecting means and to make the result of analysis displayed on the display means; wherein the display means displays the parameter used for the estimation of the characteristic and the result of analysis.

4 Claims, 8 Drawing Sheets

(51) Int. Cl.
- *A61B 8/08* (2006.01)
- *A61B 8/13* (2006.01)
- *G06T 7/00* (2006.01)

(52) U.S. Cl.
CPC ............... *A61B 8/485* (2013.01); *A61B 8/5223* (2013.01); *G06T 7/0012* (2013.01); *G06T 2207/10136* (2013.01)

(56) References Cited

U.S. PATENT DOCUMENTS

2007/0112267 A1* 5/2007 Matsumura et al. .......... 600/437
2009/0143676 A1* 6/2009 Matsumura ................... 600/438
2011/0026800 A1 2/2011 Tonomura et al.

FOREIGN PATENT DOCUMENTS

| | | |
|---|---|---|
| JP | 05-317313 | 12/1993 |
| WO | WO 03/015635 | 2/2003 |
| WO | WO 2005/025425 | 3/2005 |

OTHER PUBLICATIONS

Chinese Office Action, Issuing Date: Jan. 12, 2012, Application No. 200980111209.2, pp. 1-3.

* cited by examiner

ULTRASONIC DIAGNOSTIC ARRANGEMENTS SELECTING PARAMETERS FOR SELECTING RELEVANT ESTIMATION DATA FOR CLASSIFYING AN ELASTICITY IMAGE

CROSS REFERENCE TO RELATED APPLICATION

This is a divisional of U.S. application Ser. No. 12/935,694, filed Sep. 30, 2010. This application relates to and claims priority from Japanese Patent Application No. 2008-089328, filed on Mar. 31, 2008. The entirety of the contents and subject matter of all of the above is incorporated herein by reference.

TECHNICAL FIELD

The present invention relates to an ultrasonic diagnostic apparatusic diagnostic apparatus for obtaining a tomogram for a diagnosis site in an object to be examined by using ultrasonic waves, and particularly to an ultrasonic diagnostic apparatusic diagnostic apparatus that can calculate distortion and/or elasticity modulus of each point on an image from RF signal frame data which are arranged in time series and display hardness or softness of a biomedical tissue as an elasticity image.

BACKGROUND ART

A conventional general ultrasonic diagnostic apparatusic diagnostic apparatus includes ultrasonic wave transmitting/receiving means for transmitting and receiving ultrasonic waves to/from an object, ultrasonic wave transmission/reception control means for controlling transmission/reception of ultrasonic waves, cross-sectional scanning means for repetitively obtaining tomogram data in the object containing a motional tissue at a predetermined period by using a reflection echo signal from the ultrasonic wave receiving means, and image display means for displaying time-series tomogram data obtained by the cross-sectional scanning means. The structure of the biomedical tissue in the object is displayed as a B mode image, for example.

Furthermore, an ultrasonic diagnostic apparatusic diagnostic apparatus that can obtain and display elasticity data of an object's tissue has been recently developed (for example, patent document 1). According to the ultrasonic diagnostic apparatusic diagnostic apparatus as described above, external force is applied from the body surface of an object to an ultrasonic wave transmitting/receiving face of an ultrasonic probe by a manual method to press a biomedical tissue, and displacement of each point is measured by using a correlation calculation of ultrasonic wave reception signals of two frames which are adjacent to each other in time series (continuous two frames). This displacement is spatially differentiated to measure distortion, and the data of the distortion is imaged. Furthermore, elasticity modulus data of the biomedical tissue represented by Young's modulus or the like are imaged from the stress distribution caused by the external force and the distortion data. The hardness or softness of the biomedical tissue can be displayed with an elasticity image based on the distortion data and the elasticity modulus data (hereinafter referred to as elasticity frame data) as described above.

The technique of obtaining the elasticity image described above has been expected to be applied to not only diagnosis of tumor mass type lesion such as cancer or the like, but also diagnosis of diffuse disorder. In the case of a structure that local indurated tissues such as knot or the like are scattered in a surrounding soft tissue in diffuse disorder, an elasticity image obtained by applying the above technique has a dapple pattern which reflects an inhomogeneous structure. When a disorder proceeds, for example, from hepatitis to cirrhosis and thus fibrosis proceeds, the knot expands into the liver parenchyma and the dapple pattern of the elasticity image is complicated. An examiner can estimate a progress state of a disorder on the basis of the state of the dapple pattern.
Patent Document 1: JP-A-5-317313

DISCLOSURE OF THE INVENTION

Problem to be Solved by the Invention

According to the above-described ultrasonic diagnostic apparatusic diagnostic apparatus that can display the elasticity image, an examiner visually checks a displayed elasticity image to estimate the progress state of a disorder. However, the visual check causes dispersion of an estimation result of the disorder among examiners, and thus there has been desired a method of objectively estimating the progress state of a disorder from image information of an elasticity image.

Therefore, the present invention has an object to provide an ultrasonic diagnostic apparatus that can present objective estimation information on the basis of an elasticity image, and specifically to provide an ultrasonic diagnostic apparatus that can classify an elasticity image by using elasticity data of the elasticity image and image information and present information which estimates the progress state of a disorder.

Means of Solving the Problem

In order to solve the above problem, an ultrasonic diagnostic apparatus according to the present invention has ultrasonic wave transmitting/receiving means configured to transmit/receive ultrasonic waves into an object; tomogram constructing means configured to generate a tomogram on the basis of RF signal frame data from the inside of the object which is received by the ultrasonic wave transmitting/receiving means, elasticity information calculating means configured to calculate elasticity data of a biomedical tissue of the object by using the RF signal frame data; elasticity image constructing means configured to generate an elasticity image on the basis of the elasticity data calculated by the elasticity information calculating means; and display means configured to display the tomogram and/or the elasticity image, and is characterized by further including: estimation data generating means configured to generate estimation data for estimating the structure of the biomedical tissue on the basis of the elasticity image, and classifying means configured to classify the elasticity image by using estimation data generated by the estimation data generating means and displaying a classification result on the display means.

Furthermore, a tissue analyzing tool according to the present invention is an analyzing tool for analyzing lesion information of a tissue of the object by using RF signal frame data obtained from the inside of the object, and is characterized by including: displacement data calculating means configured to calculate displacement data by using two or more RF signal frame data obtained in time-series; elasticity data calculating means configured to calculate elasticity data including distortion and/or elasticity modulus at each point of a cross-section of an object as an examination target by using the displacement data; elasticity image generating means configured to generate elasticity image data of the cross-section of the object from the elasticity data; estimation data generating means configured to generate the elasticity data and an elasticity image and generating plural estimation data containing a histogram of the elasticity data, statistical processing data and complexity of a diseased tissue; estimation data selecting means configured to select at least one of the plural estimation data; and classifying means configured to classify the elasticity image into any one of plural groups by using the estimation data selected by the estimation data selecting means.

Effect of the Invention

According to the ultrasonic diagnostic apparatus of the present invention, a progress state, etc. of a disorder can be objectively estimated.

DESCRIPTION OF REFERENCE NUMERALS 1 ultrasonic wave transmission/reception controller, 2 transmitter, 3 probe, 4 receiver, 5 phasing and adding unit, 6 signal processor, 7 monochromatic scan converter, 8 RF frame data selecting unit, 9 displacement measuring unit, 10 elasticity data calculator, 11 elasticity image estimating unit, 12 image classifying unit, 13 color scan converter, 14 switching and adding unit, 15 image display unit, 16 controller, 17 input device, 111 histogram calculator, 112 statistical processor, 113 detection region estimating unit, 121 estimation data selecting unit, 122 memory, 123 multivariate analysis unit

MODE FOR CARRYING OUT THE INVENTION

Figure 1:
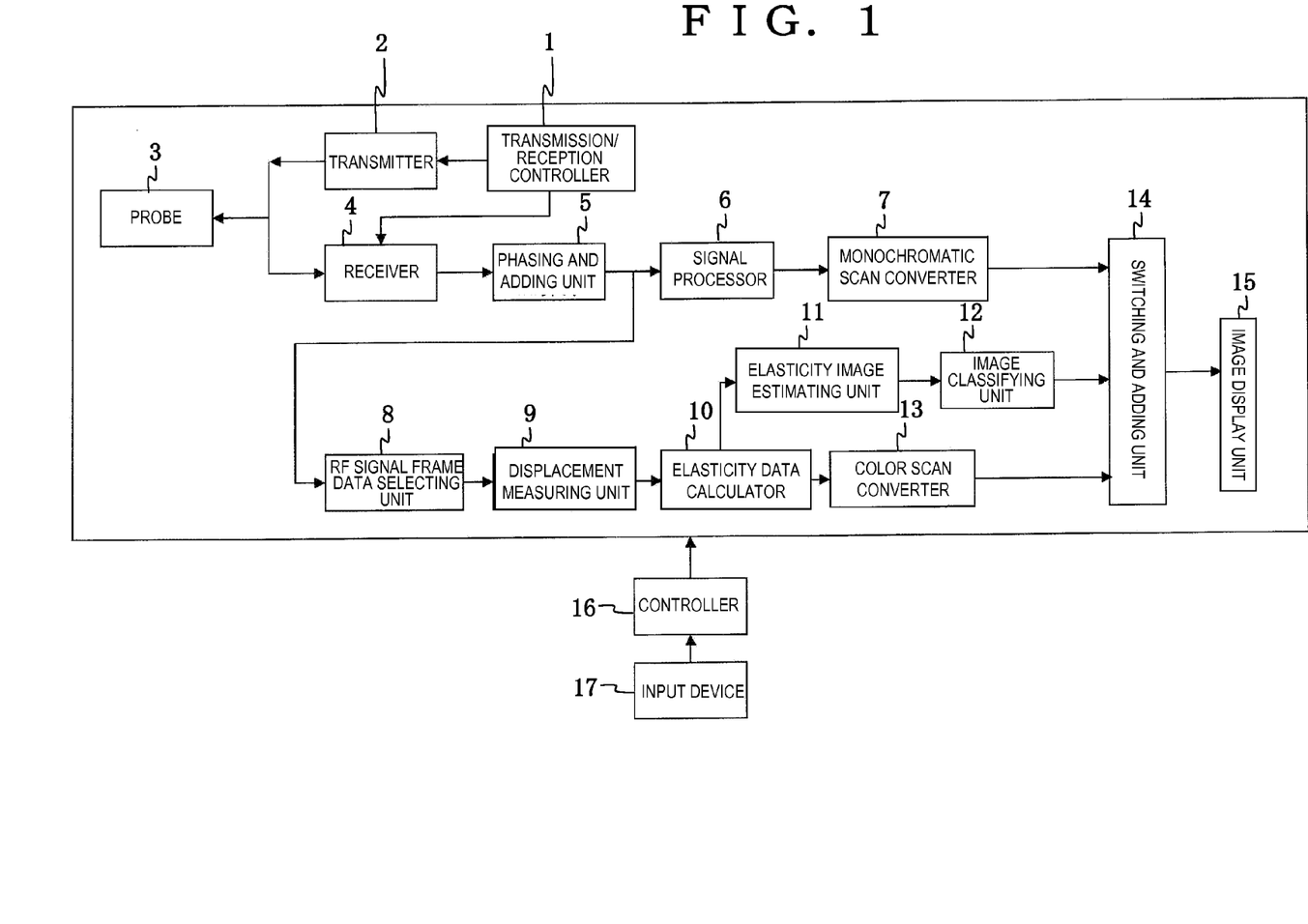
FIG. 1 is a diagram showing the overall construction of an embodiment of an ultrasonic diagnostic apparatus according to the present invention.

An embodiment according to the present invention will be described with reference to the accompanying drawings. FIG. 1 is a block diagram showing an embodiment of an ultrasonic diagnostic apparatus according to the present invention.

As shown in the figure, the ultrasonic diagnostic apparatus has, as main constituent elements, an ultrasonic wave transmission/reception controller 1, a transmitter 2, an ultrasonic probe 3, a receiver 4, a phasing and adding unit 5, a signal processor 6, a monochromatic scan converter 7, an RF signal frame data selecting unit 8, a displacement measuring unit 9, an elasticity data calculator 10, an elasticity image estimating unit 11, an image classifying unit 12, a color scan converter 13, a switching and adding unit 14, an image display unit 15, a controller 16 and an input device 17 such as a keyboard or the like.

The ultrasonic diagnostic apparatus is properly operated by an external operator through the input device 17 and the controller 16.

The signal processor 6 and the monochromatic scan converter 7 constitute a tomogram constructing unit for generating a tomogram to generate a tomogram of B mode or the like. The RF signal frame data selecting unit 8, the displacement measuring unit 9, the elasticity data calculator 10 and the color scan converter 13 constitute an elasticity image constructing unit for generating an elasticity image, and the elasticity image estimating unit 11 and the image classifying unit 12 construct an elasticity image analyzing unit. The ultrasonic diagnostic apparatus is characterized by having a function of automatically analyzing an elasticity image by the elasticity image analyzing unit and displaying the result thereof. In this embodiment, the function of the elasticity image analyzing unit is implemented by an in-computer program installed in the ultrasonic diagnostic apparatus. Independently of the ultrasonic diagnostic apparatus, a computer implementing the function of the elasticity image analyzing unit may be provided.

The ultrasonic wave transmission/reception controller 1 controls the transmitter 2 and the receiver 4 to transmit an ultrasonic wave to an examination target through the ultrasonic probe 3 and controls the timing at which an ultrasonic wave reflected from the examination target is received.

The ultrasonic probe 3 is formed by arranging many transducers in a strip shape, and it performs mechanically or electronically beam scanning to transmit and receive an ultrasonic wave to and from an object. As not shown, a transducer which serves as an ultrasonic wave generating source and also receives a reflection echo is contained in the ultrasonic probe 3. Each transducer has a function of converting an input wave transmission signal of a pulse wave or continuous wave to an ultrasonic wave and emitting the ultrasonic wave, and a function of receiving an ultrasonic wave emitted from the inside of the object, converting the ultrasonic wave to a reception signal of an electrical signal and outputting the reception signal.

The ultrasonic probe 3 constitutes a press face for applying a press operation to an object when an ultrasonic wave is received/transmitted. Therefore, a press plate is mounted on an ultrasonic wave transmitting/receiving face of the ultrasonic probe 3. The press plate is brought into contact with the body surface of the object, and the press face is manually moved upwardly and downwardly to press the object, whereby a stress distribution is effectively applied to the inside of the body cavity of a diagnosis site of the object. The press plate may be provided with a pressure sensor. In place of the manual press operation, press based on heart stroke or beat of artery may be used. In this case, the press plate may be omitted.

The transmitter 2 generates a wave transmission pulse for driving the ultrasonic probe 3 to generate an ultrasonic wave, and also sets the convergence point of the ultrasonic wave transmitted by a built-in wave transmitting phasing and adding unit to some depth.

The receiver 4 amplifies a reflection echo signal received by the ultrasonic probe 3 with a predetermined gain. Amplified wave reception signals whose number corresponds to the number of respective transducers are input to the phasing and adding unit 5 as wave reception signals which are independent of one another. The phasing and adding unit 5 phases and then adds wave reception signals amplified by the receiver 4, and outputs RF signal frame data at a predetermined frame rate.

The signal processor 6 receives the wave reception signal (RF signal frame data) from the phasing and adding unit 5 to perform various kinds of signal processing such as gain correction, log correction, wave detection, edge enhancement, filter processing, etc.

The ultrasonic probe 3, the ultrasonic wave transmission/reception controller 1, the wave transmitting unit 2, the receiver 4, the phasing and adding unit 5 and the signal processor 6 constitute the ultrasonic wave transmitting/receiving means, and an ultrasonic beam is scanned in a fixed direction in the body of the object by using the ultrasonic transducer 3 to obtain one tomogram.

The monochromatic scan converter 7 has cross-section scanning means for reading out RF signal RF signal frame data output from the signal processor 6 of the ultrasonic wave transmitting/receiving means described above at a period of a television system and means for controlling the system. Specifically, it contains an A/D converter for converting a reflection echo signal from the signal processor 6 to a digital signal, plural frame memories for storing tomogram data digitalized by the A/D converter in time-series, and a controller for controlling the above operations.

In this embodiment, the RF signal frame data selecting unit 8, the displacement measuring unit 9, the elasticity data calculator 10 and the color scan converter 13 constituting the elasticity image constructing unit are provided while branched from the output side of the phasing and adding unit 5, and the switching and adding unit 14 is provided at the output side of the monochromatic scan converter 7 and the color scan converter 13.

The RF signal frame data selecting unit 8 has a frame memory for successively securing RF signal frame data which are successively output from the phasing and adding unit 5 with time at a frame rate of the ultrasonic diagnostic apparatus, selects one RF signal frame data from plural RF signal frame data which were secured in the past, and outputs to the displacement measuring unit 9 a pair of the selected RF signal frame data and RF signal frame data which is newly secured in the frame memory. A criterion for selecting one RF signal frame data from the past RF signal frame data is given on the basis of an instruction from the controller 16. For example, an operator may specify a specific time before the press operation is started, and select RF signal frame data obtained at that time, or when the press operation is automatically executed according to beat or the like, a no-press state may be automatically determined on the basis of beat, and the RF signal frame data obtained under this state may be selected.

It is described that the signal output from the phasing and adding unit 5 is RF signal frame data, however, the signal may be a signal based on the format of I, Q signal obtained by subjecting an RF signal to complex demodulation, for example.

The displacement measuring unit 9 executes one-dimensional or two-dimensional correlation processing on a pair of RF signal frame data output from the RF signal frame data selecting unit 8, and measures a displacement or moving vector (the direction and magnitude of the displacement) at each measurement point on the tomogram to generate displacement frame data and correlation frame data. A block/matching method or a gradient method as described in the patent document 1 is known as a method of detecting the moving vector. According to the block/matching method, an image is divided into blocks each of which includes N×N pixels, for example, a block which is most approximate to a block being noted in a present frame is searched from a previous frame, and a predictive coding is performed by referring to the searched block.

The elasticity data calculator 10 calculates a distortion amount, an elasticity modulus or the like of each measurement point on a tomogram from the displacement frame data output from the displacement measuring unit 9 to generate numerical value data (elasticity frame data) of the distortion amount or the elasticity modulus, and outputs the numerical value data to the color scan converter 13. The distortion amount is an index representing the hardness of a tissue, and when the thickness of a predetermined region at an initial stage (under no-press state) is represented by D and a compression amount based on press is represented by $\Delta d$, it is represented by $\Delta d/D$. For example, it can be calculated by spatially differentiating the displacement of each point in the depth direction. The elasticity modulus is represented by Young's modulus, modulus of rigidity, modulus of volume elasticity or the like. For example, the Young's modulus Ym is calculated by dividing stress (pressure) at each calculation point by a distortion amount at each calculation point as shown in the mathematical expression (1).

$$Ym(i,j) = \text{pressure}(i,j)/\text{distortion amount}(i,j) \quad (1)$$

In the mathematical expression, i,j represent the coordinate of frame data and i,j=1, 2, 3, ....

Furthermore, the pressure applied to the body surface may be measured according to a method of interposing a pressure sensor at the contact face between the body surface and the press mechanism and directly measuring the pressure through the pressure sensor, or a method of detecting distortion of a deformed body for pressure measurement through signal processing as in the case of a method described in JP-A-2005-66041.

The elasticity data calculator 10 may subject the calculated elasticity frame data to various image processing such as smoothing processing, contrast optimizing processing within the coordinate plane, smoothing processing in the time-axis direction between frames, etc., and output the post-processing elasticity frame data as a distortion amount.

The color scan converter 13 reads out the elasticity frame data transmitted from the elasticity data calculator 10 at a period of a television system, applies predetermined color or gradation in accordance with the value of the elasticity data to obtain image data and displays the image data on the display unit 15 through the switching and adding unit 14.

Figure 2:
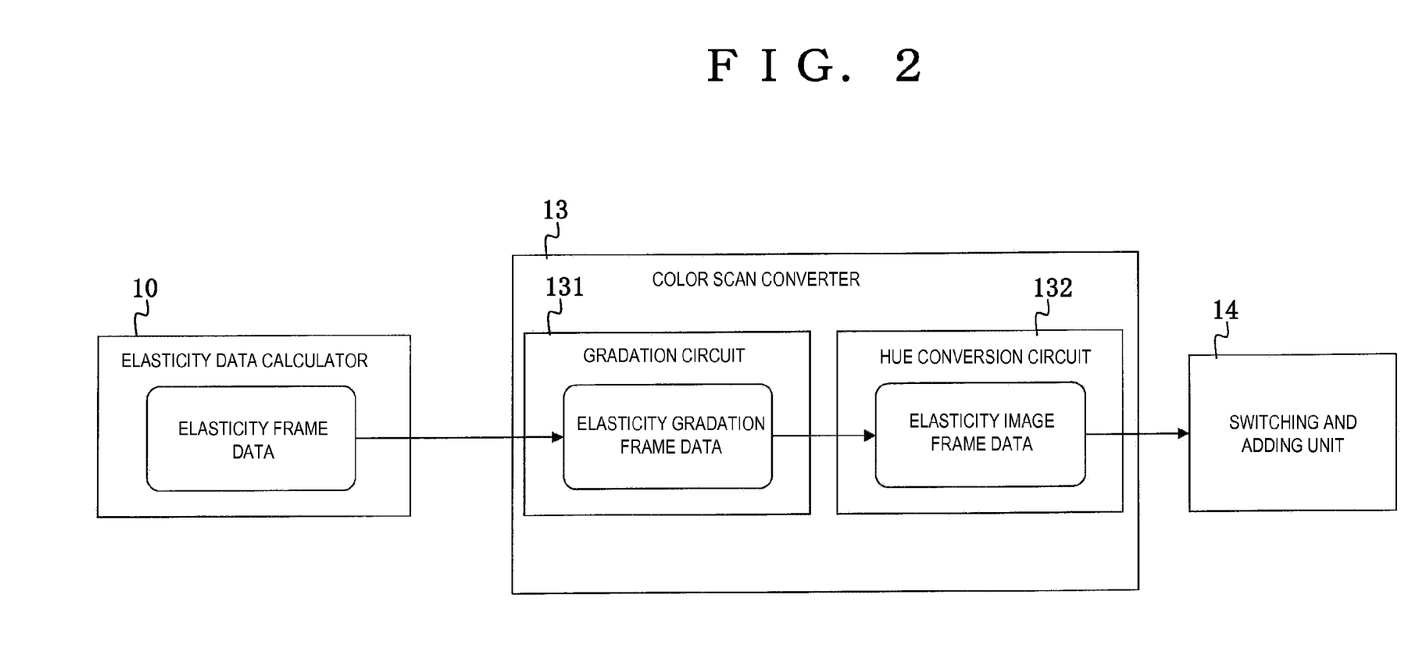
FIG. 2 is a diagram showing the construction of a color scan converter of the ultrasonic diagnostic apparatus of FIG. 1.

FIG. 2 shows an example of the construction of the color scan converter 13. In the example of FIG. 2, the color scan converter 13 includes a gradation circuit 131 and a hue conversion circuit 132.

The gradation circuit 131 gradates the elasticity frame data output from the elasticity data calculator 10. With respect to the gradation, for example, a range to be gradated in the elasticity frame data and upper and lower limit values thereof are input from the elasticity data calculator 10 or the controller 16, and the element data of the selected range are converted to plural levels (for example, 255 levels) in accordance with the value of the element data of the elasticity frame data within the selected range to generate elasticity gradated frame data. The region to be gradated, that is, the selected range is set within a region of interest (ROI) set by the controller 16, and it may be freely changed by an operator. The upper and lower limit values of the gradation are output from the elasticity data calculator 10 or determined on the basis of an instruction from the controller 16.

For example, when the elasticity data corresponds to the distortion amount, with respect to a region whose distortion is measured as being great in the elasticity gradation frame data, the hue conversion circuit 132 converts the region concerned in the elasticity image frame data to a red-color code. Conversely, with respect to a region whose distortion is measured as being small, the hue conversion circuit 132 converts the region concerned in the elasticity image frame data to a blue-color code.

The color scan converter 13 may be a monochromatic scan converter. With respect to the region whose distortion is measured as being great, the brightness of the region concerned in the elasticity image data may be made higher. Conversely, with respect to the region whose distortion may be measured as being small, the brightness of the region concerned in the elasticity image data may be made lower.

The switching and adding unit 14 receives monochromatic tomogram data from the monochromatic scan converter 7 and elasticity image data output from the color scan converter 13, and adds or switches both the images. Accordingly, only one of the monochromatic tomogram data and the color elasticity image data can be output, or both the image data can be additionally combined with each other and then output. Furthermore, as described in JP-A-2004-135929, the color tomographic image may be translucently superimposed on the monochromatic tomogram and displayed.

The image display unit 15 displays time-series tomogram data obtained by the monochromatic scan converter 7, that is, B-mode tomogram and an elasticity image obtained by the color scan converter 13, and it includes a D/A converter for converting image data output from the monochromatic scan converter 7 and/or the color scan converter 13 through the switching and adding unit 14 to an analog signal, and a color television monitor which receives an analog video signal from the D/A converter and displays it as an image.

An analysis result of the elasticity image analyzing unit as well as the tomogram and the elasticity image described above are displayed on the image display unit 15.

When the signal processor 6 has a function of extracting higher harmonic wave components of a reception signal and a function of extracting Doppler components, a tissue harmonic tomogram obtained by imaging higher harmonic wave components of the reception signal and a tissue Doppler image may be displayed in addition to a general B-mode image.

The elasticity image estimating unit (estimation data generating means) 11 and the image classifying unit 12 constituting the elasticity image analyzing unit receive the elasticity frame data output from the elasticity data calculator 10, and execute objective estimation/classification on the elasticity frame data. The details of the elasticity image estimating unit 11 and the image classifying unit 12 will be described in detail with reference to FIGS. 3 to 5.

Figure 3:
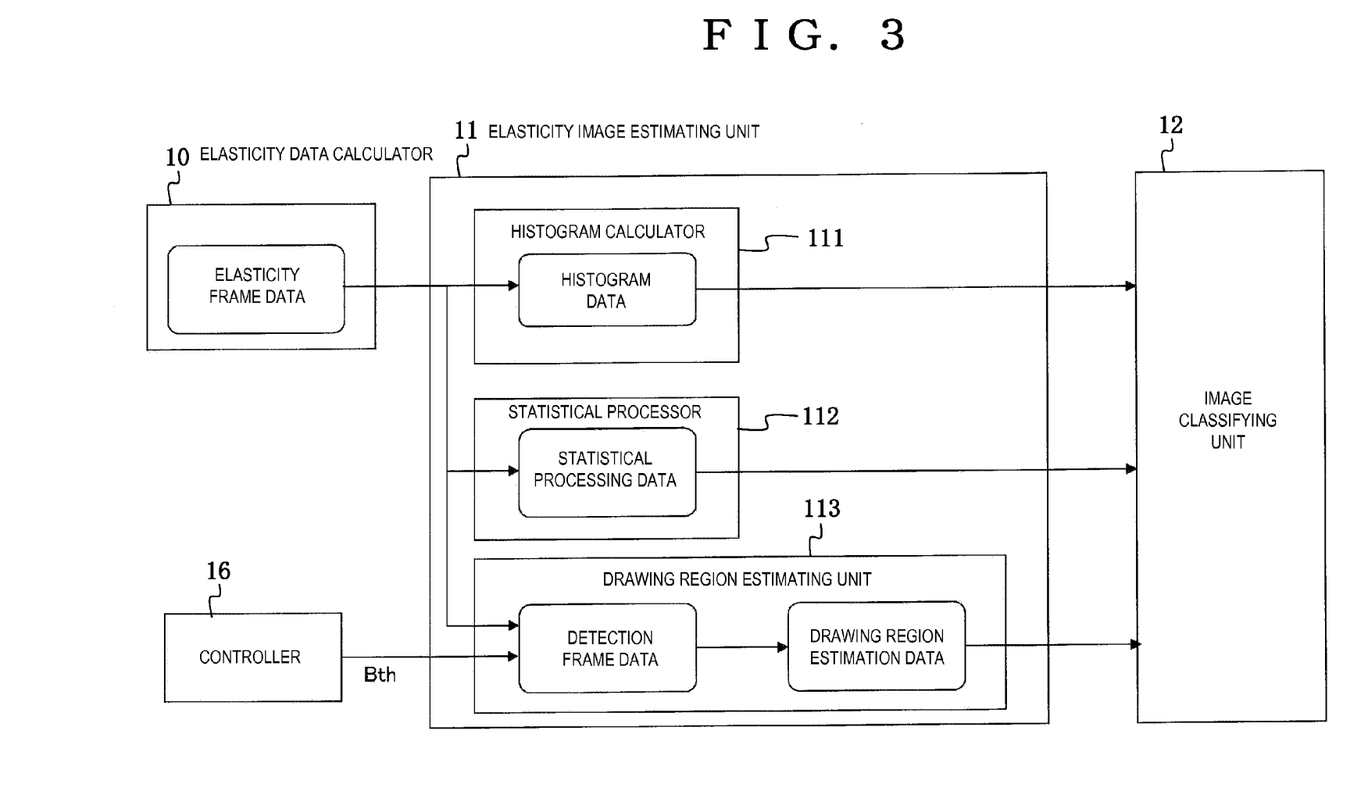
FIG. 3 is a diagram showing the construction of an elasticity image estimating unit of the ultrasonic diagnostic apparatus of FIG. 1.

The elasticity image estimating unit 11 includes a histogram calculator 111, a statistical processor 112 and a drawing region estimating unit 113 as shown in FIG. 3, and calculates estimation data serving as an index when an elasticity image drawn on the basis of elasticity frame data is classified into any one of plural groups in the image classifying unit 12.

The histogram calculator 111 counts a distortion amount or an appearance frequency of elasticity modulus from the elasticity frame data output from the elasticity data calculating circuit 10 and creates histogram data. The histogram corresponds to the distribution of tissues which are different in hardness in the elasticity image, and it also serves as an index for image classification. However, according to this embodiment, in order to set the histogram as numeric data which is used for automatic classification in the image classifying unit 12, the distortion degree (skewness), sharpness, etc. of the histogram are calculated.

Figure 4:
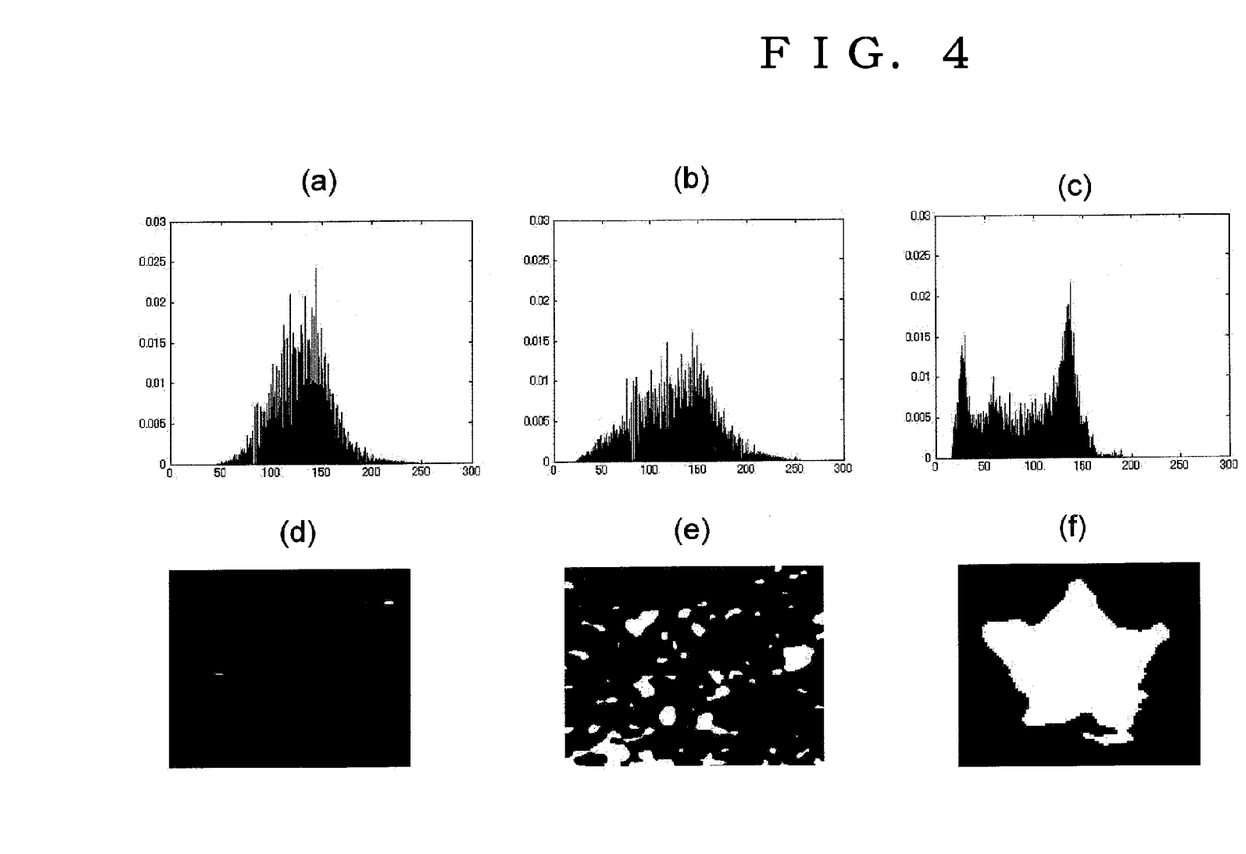
FIG. 4 is a diagram showing an analysis example of the elasticity image estimating unit.

FIG. 4 shows an analysis example of the elasticity image estimating unit 11 using a phantom. FIG. 4(a) to (c) are diagrams showing histograms of the distortion amount obtained from the elasticity frame data measured by the ultrasonic diagnostic apparatus using a phantom, wherein FIG. 4(a) shows an example in which a phantom imitating an uniform tissue is used, FIG. 4(b) shows an example in which a phantom containing scattered inclusions, and FIG. 4(c) shows an example in which a phantom containing a star-shaped inclusion. As shown in FIGS. 4(a) to 4(c), with respect to the uniform phantom, the shape of the histogram is symmetrical. However, when there is some inclusion, the symmetric property is low. The distortion degree or the sharpness of the histogram as described above can be digitalized to obtain estimation data according to the following mathematical expressions (2), (3) ((arithmetical expression 1), (arithmetical expression 2)).

[Arithmetical Expression 1]

$$\text{Distortion Degree Skewness} = \frac{1}{n}\sum_{i=1}^{n}\left(\frac{x_i - \bar{x}}{\sigma}\right)^3 \qquad (2)$$

[Arithmetical Expression 2]

$$\text{Sharpness Kurtosis} = \frac{1}{n}\sum_{i=1}^{n}\left(\frac{x_i - \bar{x}}{\sigma}\right)^4 \qquad (3)$$

In the expressions (2) and (3), n represents the number of samples, x (with overbar) represents an average and σ represents a standard deviation.

The statistical processor 112 calculates statistical processing data such as the average value, the standard deviation, etc. of the elasticity frame data (distortion or elasticity modulus) described above, and digitalizes the distortion amount or the distribution of the elasticity modulus. The elasticity frame data are data including elasticity data (distortion amount or elasticity modulus) at each point of the coordinate (i,j) of the frame data, and the average value is obtained by dividing the total of the elasticity data of the respective points by the number of points.

First, the drawing region estimating unit 113 binarizes the elasticity frame data on the basis of a binarization threshold value Bth to create detection frame data. FIG. 4(d) to (f) are diagrams showing examples of images drawn out from the detection frame data generated by the drawing region estimating unit 113 using the elasticity frame data of the above phantom. In the figures, a region drawn with white is an estimation target region (for example, a region in which a lesion occurs). Subsequently, the number of regions drawn with white, the area of the regions, complexity of the shape etc. are calculated in the binarized image. With respect to the area, the ratio (area ratio) of the area of an region (drawing region) at which the distortion amount is equal to or more than a threshold value in the binarized image to the area of the other regions is calculated.

With respect to the shape, the simplest shape is a circle, and even in the case of regions having the same area, the shape of a region which is longer in circumferential length is more complicated.

Accordingly, the degree of complexity can be defined by the following mathematical expression (4).

$$\text{Degree of Complexity} = (\text{Circumferential length})^2/\text{area} \quad (4)$$

As described above, the expansion and shape of a region having a target distortion amount or elasticity modulus (that is, a region having a distortion amount or elasticity modulus which is not less than the threshold value Bth or not more than the threshold value Bth) are digitalized, and estimation data which are used in the image classifying unit 12 described later are obtained.

The threshold value Bth can be arbitrarily set through the controller 16 by an operator, however, a threshold value which makes the degree of complexity maximum can be calculated so as to obtain a binarized image in which the drawing region is emphasized, and used.

In the elasticity image estimating unit 11, in addition to the average value and the standard deviation of the above elasticity frame data, feature quantities using a co-occurrence matrix which is general as a method of statistically calculating a texture, such as homogeneity, heterogeneity, contrast, angular secondary moment, entropy, inverse differential moment can be set as estimation data.

The various kinds of estimation data calculated in the elasticity image estimating unit 11 as described are set as indexes for classification in the image classifying unit. Furthermore, an operator can input an examination result, for example, a blood examination result through the controller 16, and add it to the indexes for estimation.

Figure 5:
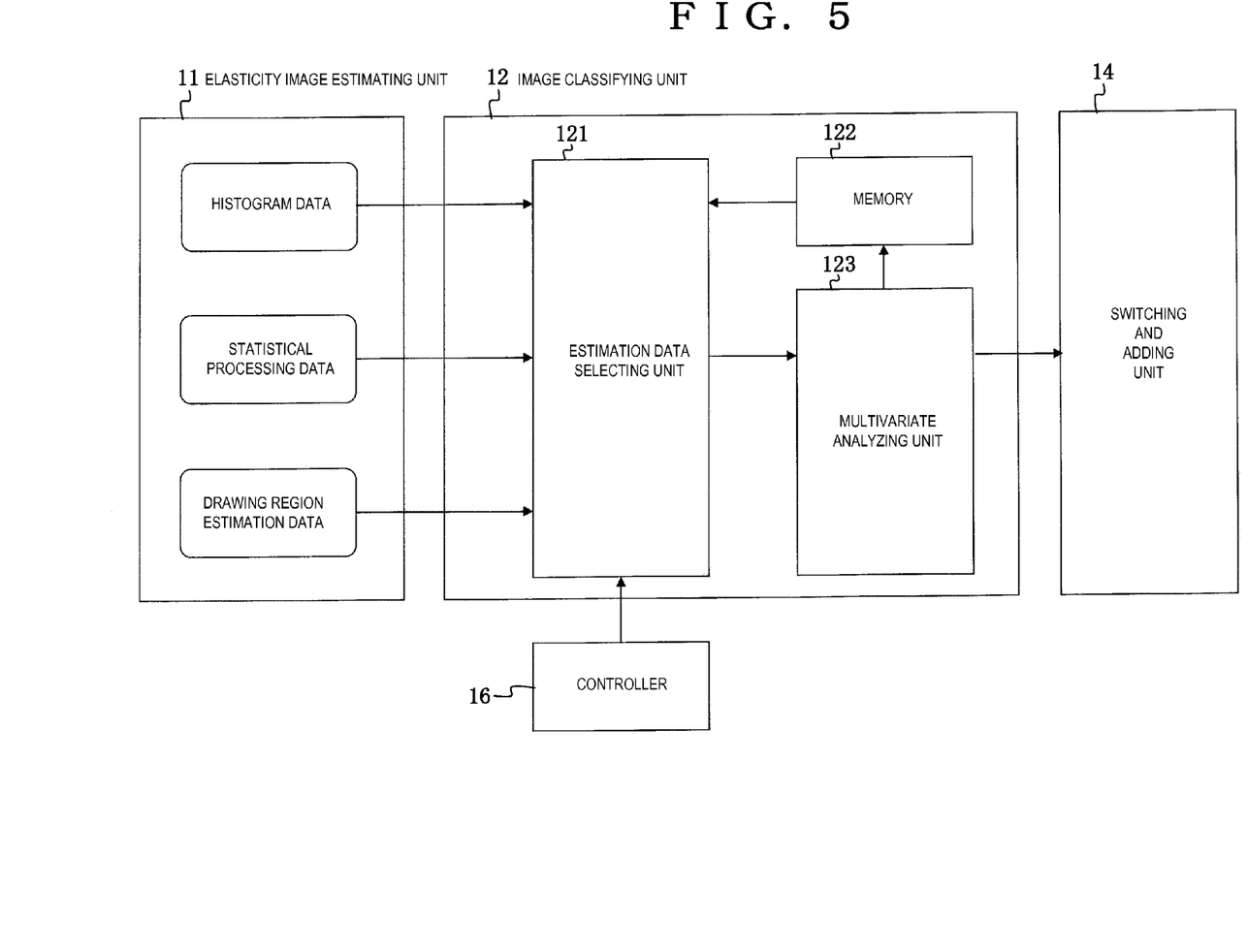
FIG. 5 is a diagram showing the construction of an image classifying unit of the ultrasonic diagnostic apparatus of FIG. 1.

The image classifying unit 12 classifies elasticity images into at least two or more groups by using at least one or more estimation data of histogram data, statistical processing data and drawing region estimation data which are calculated in the above elasticity image estimating unit 11, and has an estimation data selecting unit 121, a memory 122 and a multivariate analyzing unit 123 as shown in FIG. 5.

Figure 6:
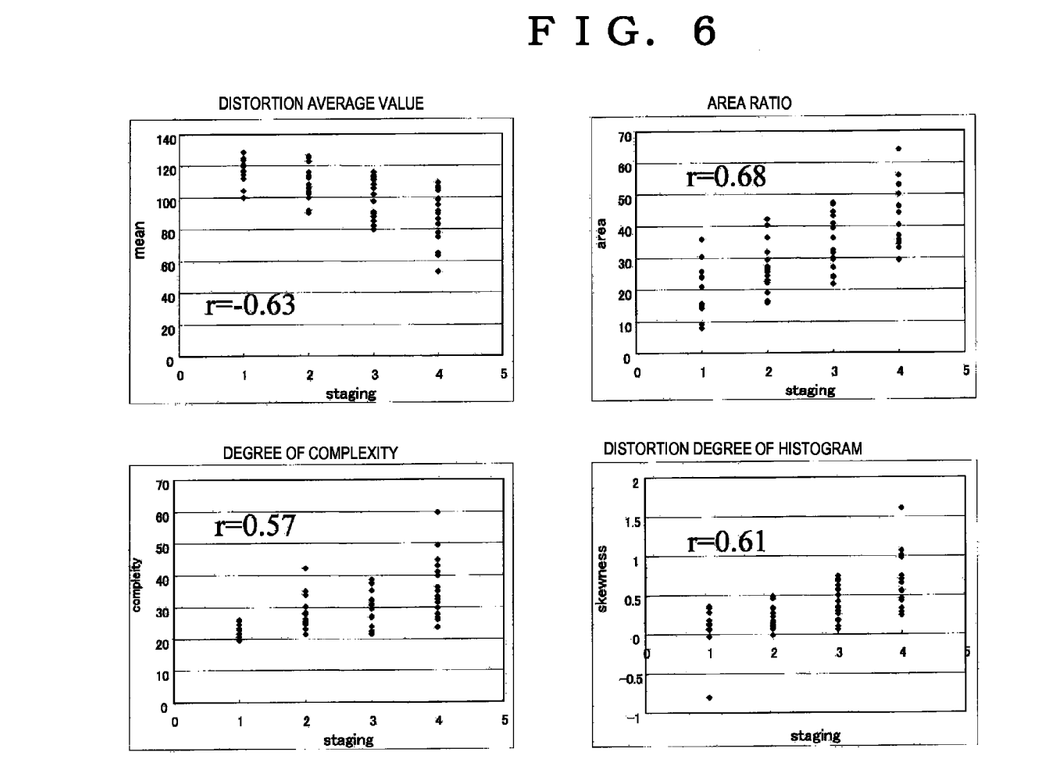
FIG. 6 is a diagram showing an example of estimation data stored in a memory of the image classifying unit.

In the memory 122 are stored elasticity image data of each group for which diagnosis is settled on the basis of a pathological diagnosis or the like, and estimation data for the elasticity image data. Diagnosis information of a new object and estimation data generated in the ultrasonic diagnostic apparatus are accumulated in the memory 122 as needed. An example of the estimation data stored in the memory is shown in FIG. 6. In FIG. 6, the average value of the distortion amount, the area ratio, the degree of complexity and the distortion degree of the histogram of the elasticity image data which are classified to every group are shown in the form of a graph every parameter. In FIG. 6, a value represented by r indicates a correlation coefficient between the parameter and the classification. As r is larger, it indicates that the parameter has a higher correlation. The calculated correlation coefficients are stored in the memory 122 every parameter.

The estimation data selecting unit 121 selects a parameter used for estimation. As a parameter selecting method is used not only a method of selecting a parameter through the controller 16 by an operator, but also a method of selecting an estimation parameter whose correlation is higher when the elasticity images of the respective groups stored in the memory 122 in the image classifying unit 12 are classified. For example, as a default, a predetermined number of parameters having high correlation with the classification are selected in turn from a higher parameter, and the selected parameter is displayed on the display unit 15. The operator arbitrarily deletes, adds or the like the selected parameter to determine a parameter to be used for classification.

The multivariate analyzing unit 123 receives estimation data of at least one or more parameters selected in the estimation data selecting unit 121, and outputs a classification result, that is, a result indicating which one of plural groups the elasticity image having the estimation data concerned belongs to.

For example, multiple linear regression analysis, discrimination analysis, principal component analysis, quantification method, factor analysis, cluster analysis, multidimensional scale method, neural network or the like is known as a method of multivariate analysis adopted by the multivariate analyzing unit 123. Any one of them can be selected, however, a classification method using perceptron of a neural network will be described hereunder.

Figure 7:
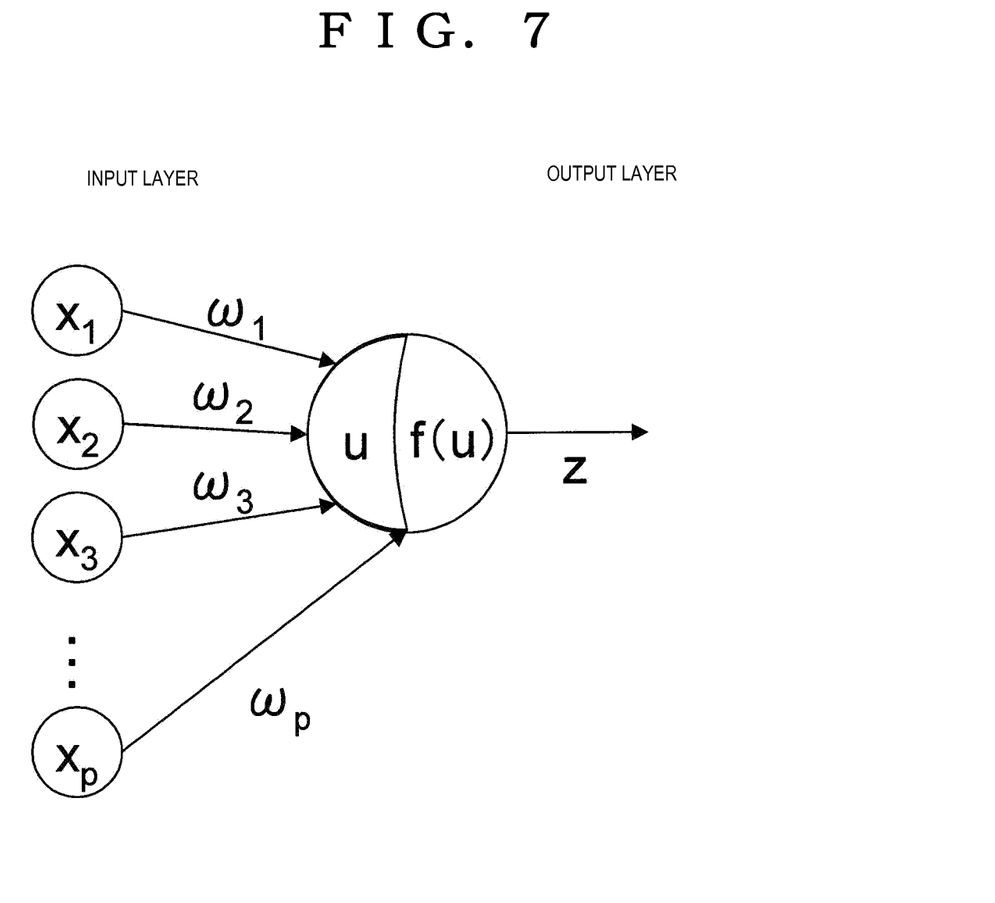
FIG. 7 is a diagram showing an example of the image classifying unit (multivariate analysis unit).

FIG. 7 shows the structure of a simple perceptron as an example of the neural network. As shown in FIG. 7, the simple perceptron includes an input layer and an output layer constructed by a simple unit (neuron). Estimation data of the parameters selected in the estimation data selecting unit 121 are input to the input layer. For example, when four parameters such as the average value and standard deviation of the distortion amount, the area ratio of the region (drawing region) having the distortion amount which is not less than the threshold value in the binarized image, and the degree of complexity are selected as the parameters, the respective values of the parameters calculated in the elasticity image estimating unit 11, that is, estimation data x1, x2, x3, x4 are input.

At the output layer, the total u of the input values xi weighted with coupling loads ωi is converted by a predetermined function f(u) according to the following mathematical expression (5) ((arithmetical expression 3)), and the value thereof is output.

[Arithmetical Expression 3]

$$u = \omega_0 + \sum_{i=1}^{i} \omega_i x_i \quad (5)$$

A threshold function or a linear function is used as the function f(u) used at the output layer. For example, in the case of the threshold function, f(u)=1 for u larger than a threshold value h, f(u)=0 for u smaller than the threshold value h, and an output value z is set to satisfy z=f(u). In the case of the linear function in which the output increases and decreases linearly to the input, the input value u is directly set as the output value.

A result of f(u)=1 means that an elasticity image for which estimation data is created belongs to a specific group, and a result of f(u)=0 means that the elasticity image concerned does not belong to any specific group. When the simple perceptron using the threshold function is used as the conversion function of the output layer, plural simple perceptrons having different threshold values of the output layer are arranged in parallel, and classified into plural groups. When the input value u corresponds to the output value, the threshold value is set in a multistage style in accordance with the number of groups, and the output value is classified into plural groups.

The perceptron is characterized in that an output signal is compared with a teacher signal (correct answer) and when they are different from each other, the coupling load ωi and the threshold value h are changed, that is, learning is performed. Specifically, when the difference between the teacher signal z* and the output value z is represented by δ, the coupling load ωi is corrected so that δ2 is minimum as shown in the mathematical expression (6) ((arithmetical expression 4)).

[Arithmetical Expression 4]

$$\omega_i \Leftarrow \omega_i + \epsilon(z^* - z)x_i \quad (6)$$

In the expression, ϵ represents a learning coefficient. For example, a diagnosis result (any one of first to N-th groups) obtained by pathologic diagnosis for an estimation target is used as the teacher signal. The learning of the perceptron as described above can be performed by using plural elasticity image data with which a diagnosis has been settled in advance and the estimation data thereof. Furthermore, it can be performed every time a correct answer (settled diagnosis result) is obtained with respect to a new classification result whereby the accuracy of the result can be enhanced.

When no teacher signal is input, a classification result is output by using the latest coupling load ωi and the threshold value h.

The classification result of the multivariate analyzing unit 123 is transmitted to the switching and adding unit 14, and displayed on the image display unit 15 together with a tomogram and an elasticity image. Any method of displaying a classified group name, plotting on a graph containing a group on the abscissa axis and an output value (u) on the ordinate axis or the like can be adopted as the display method.

According to the ultrasonic diagnostic apparatus of this embodiment, estimation data such as a histogram, statistical processing data, binarized frame data, etc. are created by using elasticity data obtained from RF frame data, and also at least one of these estimation data is selected and analyzed by multivariate analysis, whereby information which objectively represents the progress state of a disorder can be supplied.

In the above embodiment, the function of the image analyzing unit including the image estimating unit 11 and the image classifying unit 12 is described as the internal function of the ultrasonic diagnostic apparatus. However, these functions may be constructed as an image analyzing tool on a computer which is independent of the ultrasonic diagnostic apparatus. In this case, the elasticity frame data are transmitted from the ultrasonic diagnostic apparatus to the image analyzing tool, and image diagnosis can be remotely performed.

EMBODIMENT

With respect to 61 examples of liver disorders for which diagnosis is settled by pathologic diagnosis, a liver region was selected from an elasticity image obtained by the ultrasonic diagnostic apparatus, and image analysis according to the present invention was performed. That is, the average value and standard deviation of a distortion amount for a selected region, and the area ratio and complexity degree for a region which is drawn by a binarized image are calculated. Classification into each of stages such as nonfibrosis (stage 0), enlargement of fibrosis of portal area (stage 1), formation of fibrous cross-linkage (stage 2), formation of fibrous cross-linkage entailing skewness of lobule (stage 3) and cirrhosis (stage 4) is performed on the basis of the above data as the estimation data.

Figure 8:
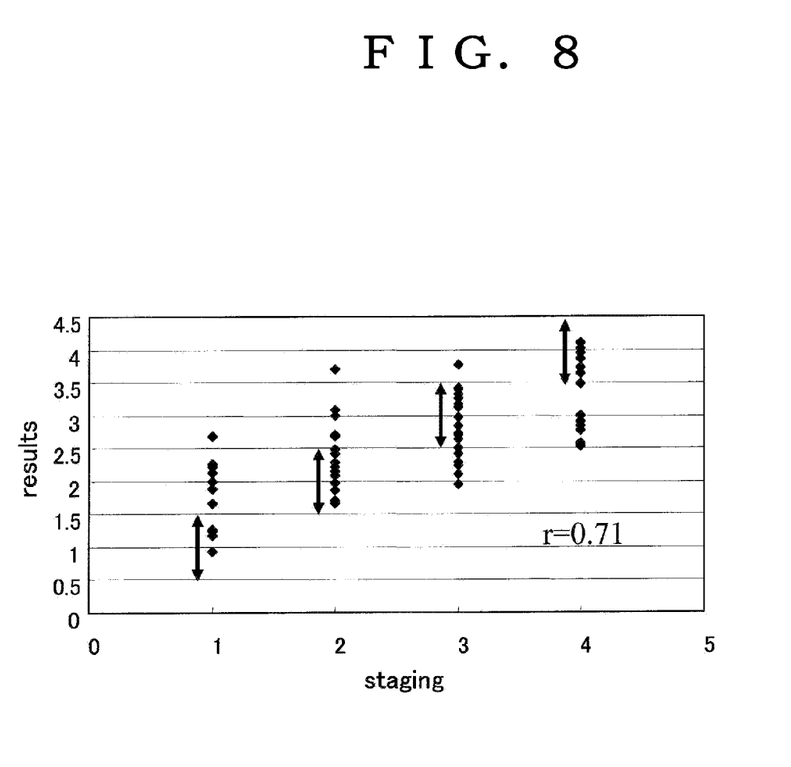
FIG. 8 is obtained by an embodiment.

A result is shown in FIG. 8. In the graph shown in FIG. 8, the abscissa axis represents the stage, and the ordinate axis represents the output (any unit) of the image classifying unit. The output value of a patient whose stage is settled on the basis of the pathologic diagnosis is plotted every stage. A range indicated by an arrow represents a range classified by the image classifying unit. The correlation between this classification result and the stage is equal to 0.71, and it has been confirmed that the correlation is remarkably higher as compared with the correlation of the individual parameters (FIG. 6).

What is claimed is:

1. An ultrasonic diagnostic apparatus having an analyzing tool for analyzing lesion information of a tissue of an object by using RF signal frame data obtained from the object and a display,
the analyzing tool comprising:
at least one computer and memory, pre-configured to effect operations including:
calculating displacement data by using RF signal frame data obtained in time-series;
calculating elasticity data including at least one of distortion and elasticity modulus at each point of a cross-section of an object as an examination target by using the displacement data;
generating elasticity image data of the cross-section of the object from the elasticity data;
analyzing the elasticity data, and generating plural estimation data containing a histogram of the elasticity data, statistical processing data and shape complexity of a diseased tissue;
selecting parameters concerning estimation data relevant for classifying the elasticity image; and
multivariate-analyzing to classify the elasticity image into two or more groups by using the estimation data of parameters selected by the estimation data selector,
wherein the display displays the elasticity image, the parameters used for classifying the elasticity image by the multivariate-analyzing, and a result of classification as classified by the multivariate-analyzing.

2. The ultrasonic diagnostic apparatus according to claim 1, wherein
the selecting is configured to contain at least an input layer and an output layer, receive plural estimation data, output a classification result, and a coupling load and a threshold value from an input to an output are changed so that a difference between the output and a teacher signal obtained from known data is corrected.

3. The ultrasonic diagnostic apparatus according to claim 1, wherein
the parameters contains an average value and a standard deviation of a distortion amount, an area ratio of a region (drawing region) whose distortion amount is not less than a threshold value in a binarized image, and a degree of complexity.

4. The ultrasonic diagnostic apparatus according to claim 1, wherein
the multivariate-analyzing performs classification by using any one of a multiple linear regression analysis, discrimination analysis, principal component analysis, quantification method, factor analysis, cluster analysis, multidimensional scale method and neural network.

* * * * *